US 7,407,667 B2
Aug. 5, 2008

(12) United States Patent
Zerrer et al.

(54) PESTICIDAL PREPARATIONS COMPRISING COPOLYMERS

(75) Inventors: Ralf Zerrer, Karlstein (DE); Gerd Roland Meyer, Frankfurt am Main (DE); Franz Xaver Scherl, Burgkirchen (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 548 days.

This patent is subject to a terminal disclaimer.

(21) Appl. No.: 10/474,559

(22) PCT Filed: Apr. 6, 2002

(86) PCT No.: PCT/EP02/03827

§ 371 (c)(1),
(2), (4) Date: Apr. 8, 2004

(87) PCT Pub. No.: WO02/089575

PCT Pub. Date: Nov. 14, 2002

(65) Prior Publication Data

US 2006/0166826 A1 Jul. 27, 2006

(30) Foreign Application Priority Data

Apr. 10, 2001 (DE) ............... 101 17 993

(51) Int. Cl.
*A01N 25/00* (2006.01)
*A01N 57/18* (2006.01)
*A61K 9/14* (2006.01)
*A61K 9/50* (2006.01)

(52) U.S. Cl. .......... 424/405; 424/489; 424/502; 504/206

(58) Field of Classification Search .......... 424/405, 424/489, 502; 504/206
See application file for complete search history.

(56) References Cited

U.S. PATENT DOCUMENTS

| 4,853,026 A | 8/1989 | Frisch et al. ........... 71/86 |
| 5,750,468 A | 5/1998 | Wright et al. ........... 504/206 |
| 5,858,921 A | 1/1999 | Magin et al. ........... 504/206 |

FOREIGN PATENT DOCUMENTS

| EP | 0 161 595 | 11/1985 |
| EP | 0 379 852 | 8/1990 |
| EP | 0 577 914 | 1/1994 |
| GB | 0 903 766 | 8/1962 |
| WO | WO 98/06259 | 2/1998 |
| WO | WO 99/05914 | 2/1999 |
| WO | WO 01/08481 | 2/2001 |

OTHER PUBLICATIONS

Derivative: Merriam Webster's Collegiate Dictionary Tenth Edition Springfield MA 1996, p. 311.*
English abstract for EP 0161595, Nov. 21, 1985.
English abstract for JP publication No. 61108781, May 27, 1986.
English abstract for CS 245183, Aug. 14, 1986.
English abstract for JP publication No. 62243888, Oct. 24, 1987.
English abstract for JP publication No. 03-097789, Apr. 23, 1991.
English abstract for JP publication No. 06-166602, Jun. 14, 1994.
English abstract for JP publication No. 11-209231, Aug. 3, 1999.
English abstract for WO 01/08481, Feb. 8, 2001.

* cited by examiner

*Primary Examiner*—Johann Richter
*Assistant Examiner*—Ernst Arnold
(74) *Attorney, Agent, or Firm*—Tod A. Waldrop

(57) ABSTRACT

The present invention relates to aqueous concentrates and solid formulations of pesticide preparations comprising copolymers which may be obtained by copolymerization of a) glycerol, b) at least one dicarboxylic acid, and c) at least one monocarboxylic acid of the formula (I)

$$R^1\text{—COOH} \qquad (I)$$

Where $R^1$ is $(C_5-C_{29})$-alkyl; $(C_7-C_{29})$-alkenyl; phenyl or naphthyl. The copolymer of the present invention increases the biological activity of the pesticide or herbicide.

23 Claims, No Drawings

PESTICIDAL PREPARATIONS COMPRISING COPOLYMERS

This Application is a 35 U.S.C. 371 of PCT/EP2002/03827 filed on Apr. 6, 2002 and claims benefit of German foreign application 101 17 993.6 filed on Apr. 10, 2001.

The invention relates to pesticide preparations comprising copolymers obtainable by copolymerization of glycerol, dicarboxylic acids and monocarboxylic acids. The copolymers effect improved bioactivity of the pesticides (herbicides, insecticides, fungicides, bactericides, molluscicides, nematicides and rodenticides).

Crop protection agents are chemical or natural substances which penetrate plant cells, plant tissue or parasitic organisms in or on the plants and damage and/or destroy them. Herbicides make up the largest proportion of pesticides, followed by insecticides and fungicides.

The most important herbicides are chemical substances which act on the transport system of plants, for example by inhibiting photosynthesis, fatty acid biosynthesis or amino acid biosynthesis, and which lead to the inhibition of germination and growth or to the death of the plants.

The bioactivity of a pesticide can be determined by reference to plant growth or to the damage of the plants caused by the effect of the active ingredient on the leaf as a function of the activity time and the active concentration.

In order to develop the optimum pesticidal action, the pesticide must wet the chlorophyll and remain there for a sufficiently long time, or penetration of the active substance through the surface of the leaf must be achieved. A general problem here is that only a fraction of the active substance developed the desired activity, i.e. is applied to harmful plants and grasses and can adhere thereto for a sufficiently long time in order to penetrate the plant cells. By far the greatest part is lost without developing its effect.

As described in a large number of patent specifications, in order to overcome this ecological and economic disadvantage, additives which improve the wettability, the solubility, the emulsifiability or the adsorption behavior of the active substance are added to the mostly aqueous pesticide formulations. In addition, additives can facilitate and accelerate penetration of the active substances through the surface of the leaf into the plant.

WO 98/06259 describes a method of assisting bioactivity of crop protection agents, according to which an aqueous surfactant solution is sprayed onto the plants as coformulation together with or after the application of the active substance. The wetting agents used are aqueous organosilicon and/or organofluorine compounds.

In EP 379 852 and U.S. Pat. No. 4,853,026 oils are added to the herbicide N-phosphonomethylglycine (glyphosate) as water-in-oil emulsions in order to improve the contact of the hydrophilic active ingredient with the lipophilic epidermis of the plants. A disadvantage is the inadequate stability of the emulsions.

According to WO 99/05914 an improvement in the action of anionic pesticides can be achieved by formulating the anionic active substance together with protonated polyamines or derivatives thereof as aqueous colloidal dispersion.

U.S. Pat. No. 5,858,921 teaches that the concentration of glyphosate can be reduced without reducing the bioactivity if water-soluble long-chain alkyldimethylamine oxides and water-soluble quaternary ammonium halides are added to the formulation.

U.S. Pat. No. 5,750,468 describes glyphosate formulations which comprise tertiary or quaternary ether amines as adjuvant.

All of the hitherto described methods for improving the bioactivity of pesticides are only successful to a limited extent. The object was therefore to develop novel compositions or formulations of pesticides, in particular of herbicides of the N-phosphonomethylglycine (glyphosate) class of substance with improved effectiveness which are at the same time cost-effective, easy to handle and well tolerated by humans and the environment. Glyphosate, being an environmentally very well tolerated and at the same time highly effective herbicide which can be used widely, is used in agriculture in large amounts. It is preferably applied as water-soluble salt, for example as alkali metal salt, ammonium salt, alkylamine salt, alkylsulfonium salt, alkylphosphonium salt, sulfonylamine salt or aminoguanidine salt or else as free acid in aqueous formulations, or else in solid form, with wetting agents to leaves and grasses, where it acts upon the transport system of the plants and destroys them.

Surprisingly, it has been found that the pesticidal action of crop protection agents is significantly improved by the addition of copolymers obtainable by copolymerization of glycerol, dicarboxylic acid(s) and monocarboxylic acid(s).

The crosslinking of the polyglycerols by means of dicarboxylic acid(s) leads to network-like condensation products. Surprisingly, the crosslinked polyglycerols exhibit a markedly higher effectiveness than uncrosslinked polyglycerols.

The effectiveness can be influenced in a targeted manner via the degree of crosslinking.

The crosslinking also advantageously effects increased electrolyte stability of the agents. Moreover, the viscosity of the agents can be set via the degree of crosslinking.

The invention provides pesticide preparations comprising at least one copolymer obtainable by copolymerization of a) glycerol b) at least one dicarboxylic acid and c) at least one monocarboxylic acid according to formula (I)

$$R^1\text{—COOH} \tag{I}$$

where $R^1$ is $(C_5\text{-}C_{29})$-alkyl; $(C_7\text{-}C_{29})$-alkenyl; phenyl or naphthyl.

The alkyl or alkenyl radicals $R^1$ may be linear or branched. The phenyl or naphthyl radicals may be substituted, preferred substituents being $(C_1\text{-}C_6)$-alkyl, $(C_1\text{-}C_6)$-alkenyl, $(C_1\text{-}C_6)$-alkoxy, —CHO, —CO(($C_1\text{-}C_6$)-alkyl) or halogen.

Preferred dicarboxylic acids b) are oxalic acid; dicarboxylic acids according to formula (II)

$$\text{HOOC—R}^2\text{—COOH} \tag{II}$$

and/or dicarboxylic acids according to formula (III),

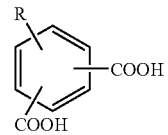

(III)

where $R^2$ is a $(C_1\text{-}C_{40})$-alkylene bridge, preferably $(C_1\text{-}C_{10})$-alkylene, particularly preferably $(C_1\text{-}C_4)$-alkylene, or a $(C_2\text{-}$ $C_{20}$)-alkenylene bridge, preferably ($C_2$-$C_6$)-alkenylene, particularly preferably $C_2$-alkenylene, and R is one or more radicals chosen from H; ($C_1$-$C_{20}$)-alkyl, preferably ($C_1$-$C_6$)-alkyl, particularly preferably ($C_1$-$C_2$)-alkyl; ($C_2$-$C_{20}$)-alkenyl, preferably ($C_2$-$C_6$)-alkenyl; phenyl; benzyl; halogen; —$NO_2$; ($C_1$-$C_6$)-alkoxy; —CHO or —CO(($C_1$-$C_6$)-alkyl). $R^2$ in formula (II) may be linear or branched.

Formula (II) also includes dimerized fatty acids, such as, for example, the Pripol acids.

Particularly preferred dicarboxylic acids b) are oxalic acid, malonic acid, succinic acid, glutaric acid, adipic acid, pimelic acid, suberic acid, fumaric acid, maleic acid, phthalic acid, isophthalic acid and/or terephthalic acid.

Particularly preferred dicarboxylic acids b) are phthalic acid, isophthalic acid and/or terephthalic acid.

A very particularly preferred dicarboxylic acid b) is phthalic acid.

Preferred monocarboxylic acids c) are those where $R^1$ is ($C_7$-$C_{22}$)-alkyl or ($C_7$-$C_{22}$)-alkenyl.

Particularly preferred monocarboxylic acids c) are saturated or unsaturated fatty acids or mixtures thereof, such as, for example, coconut acid, oleic acid, lauric acid, tridecanoic acid, myristic acid, pentadecanoic acid, palmitic acid, margaric acid, stearic acid, nonadecanoic acid, arachidic acid, behenic acid, linoleic acid, linolenic acid, palmitic acid and tallow fatty acid.

Particularly preferred monocarboxylic acids c) are coconut acid and tallow fatty acid.

A very particularly preferred monocarboxylic acid c) is coconut acid.

Particularly advantageous copolymers are those obtainable by copolymerization of glycerol, phthalic acid and coconut acid.

Preferably, the copolymers comprise 19.9 to 99% by weight of structural units originating from component a), 0.1 to 30% by weight of structural units originating from component b) and 0.9 to 80% by weight of structural units originating from component c).

The copolymers particularly preferably comprise 50 to 90% by weight of structural units originating from component a), 1 to 25% by weight of structural units originating from component b) and 2 to 49% by weight of structural units originating from component c).

A content of from 1 to 10% by weight of structural units originating from component b) is particularly advantageous for the properties of the copolymers.

The copolymers advantageously have an OH number of from 400 to 1000 mg of KOH/g (determination in accordance with DIN 53240).

The viscosity of the 100% pure copolymers, measured at 60° C. using a rotary viscometer, is advantageously in the range from 1500 mPas to 35000 mPas. Higher viscosities are possible, but hinder handling of the substances. The copolymers are advantageously handled as 75 to 90% strength by weight aqueous solution.

The copolymers are obtainable by copolymerization of
a) glycerol
b) at least one dicarboxylic acid and
c) at least one monocarboxylic acid according to formula (1).

The copolymerization is preferably carried out by firstly polymerizing the glycerol component a) to give polyglycerol and then copolymerizing the polyglycerol and a mixture of dicarboxylic acid component b) and monocarboxylic acid component c).

In another preferred variant, the glycerol component a) is firstly polymerized to give polyglycerol, then the dicarboxylic acid component b) is copolymerized and then the monocarboxylic acid component c) is copolymerized.

In a likewise preferred variant, the glycerol component a) is firstly polymerized to give polyglycerol, then the monocarboxylic acid component c) is copolymerized and then the dicarboxylic acid component b) is copolymerized.

However, the copolymerization is not limited to the above variants.

For example, variants in which some of the glycerol a) is polymerized to oligomers and then the dicarboxylic acid component b), the monocarboxylic acid component c) and the remaining glycerol a) copolymerized may also be advantageous.

Advantageous embodiments of the copolymerization are described by way of example below.

A) Polymerization of the Glycerol to Oligoglycerols or Polyglycerol:

The polymerization of the glycerol to oligoglycerols or polyglycerols can take place as standard in a stirred apparatus with water separator at 240 to 270° C. and with nitrogen introduction. The catalyst used is 50% strength sodium hydroxide solution in a concentration range from 0.1 to 0.4% by weight. After 5 to 20 hours, depending on the desired degree of polymerization, the polymerization is ended. A sample is taken and the OH number is determined. The average molar mass of the oligoglycerols or polyglycerols can be calculated from the OH number.

B) One-Pot Process with Prepolymerized Polyglycerol:

The polyglycerol is mixed in the molten state in a stirred container with water separator with the dicarboxylic acid and the monocarboxylic acid in the desired molar ratio and heated, with stirring, for 7 hours at 200-240° C. The acid number of the finished product is less than 1 mg of KOH/g.

C) Polyglycerol is Firstly Copolymerized (Crosslinked) with the Dicarboxylic Acid and then Copolymerized with the Monocarboxylic Acid:

The polyglycerol is mixed in the molten state in a stirred container with water separator with the dicarboxylic acid in the desired molar ratio and heated, with stirring, for 2 hours at 200-240° C. The resulting product is clear and homogenous. The monocarboxylic acid is then added and esterified for 5 hours at 200-240° C. The acid number of the end-product is less than 1 mg of KOH/g.

D) Polyglycerol is Firstly Copolymerized with the Monocarboxylic Acid and then Copolymerized (Crosslinked) with the Dicarboxylic Acid:

The polyglycerol is mixed in the molten state in a stirred container with water separator with the monocarboxylic acid in the desired molar ratio and heated, with stirring, for 5 hours at 200 to 240° C. The resulting product has an acid number <1 mg of KOH/g. The dicarboxylic acid is then added in the desired molar ratio and esterified for 2 hours at 200 to 240° C. The acid number of the end-product is less than 1 mg of KOH/g.

The copolymers are suitable as adjuvants in pesticide formulation for improving the bioactivity of herbicides, insecticides, fungicides, acaricides, bactericides, molluscicides, nematicides and rodenticides.

The copolymers are preferably used in herbicide formulations.

Particularly suitable herbicides are glyphosate (N-phosphonomethylglycine) and salts and/or derivatives thereof. Examples of suitable water-soluble salts are the alkali metal salts, ammonium salts, alkylamine salts, alkylsulfonium salts, alkylphosphonium [lacuna], sulfonylamine salts or aminoguanidine salts. Examples of further suitable herbicides are acifluorfen, asulam, benazolin, bentazone, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, haloxyfop, imazapic, imazamethabenz, imazamox, imazapyr, imazaquin, imazethapyr, loxynil, MCPA, MCPB, mecoprop, methylarsenic acid/MSMA, naptalam, picloram, quinclorac, quizalofop, 2,3,6-TBA and TCA.

The pesticide preparations according to the invention can comprise the copolymers in virtually any concentration.

Particularly preferred formulations are "tank-mix" and "ready to use compositions" which comprise 0.001 to 10% by weight, preferably 0.05 to 2% by weight, of pesticide and 0.01% by weight to 10% by weight, preferably 0.1% by weight to 2% by weight, particularly preferably 0.2% by weight to 1% by weight, of copolymers. The weight ratio of copolymers to pesticide is here preferably between 1:10 and 500:1, particularly preferably 1:4 and 4:1.

Concentrate formulations which are diluted prior to use can comprise the pesticide in amounts of from 5 to 60% by weight, preferably 20 to 40% by weight, and the copolymers in amounts of from 3 to 50% by weight. The weight ratio of copolymers to pesticides is here preferably between 1:20 and 1:1, preferably 1:10 and 1:2.

Alternatively, the formulations according to the invention can be prepared in solid form as powders, pellets, tablets or granulates, which are dissolved in water prior to use. Solid preparations can comprise the pesticide in amounts of from 20 to 80% by weight, preferably 50 to 75% by weight, particularly preferably 60 to 70% by weight and the copolymers in amounts of from 5 to 50% by weight, preferably 10 to 30% by weight.

The pesticide preparations can, moreover, comprise the customary thickeners, antigelling agents, anti-freeze agents, solvents, dispersants, emulsifiers, preservatives, further adjuvants, binders, antifoams, thinners, disintegrants and wetting agents.

Thickeners which may be used are xanthan gum and/or cellulose, for example carboxy-, methyl-, ethyl- or propylcellulose. The finished compositions preferably comprise 0.01 to 5% by weight of thickeners.

Suitable solvents are monopropylene glycol, animal and mineral oils.

Suitable dispersants and emulsifiers are nonionic, amphoteric, cationic and anionic surfactants.

Preservatives which may be used are organic acids and their esters, for example ascorbic acid, ascorbyl palmitate, sorbate, benzoic acid, methyl and propyl 4-hydroxybenzoate, propionates, phenol, for example 2-phenyl phenate, 1,2-benzisothiazolin-3-one, formaldehyde, sulfurous acid and salts thereof.

Suitable antifoams are polysilicones.

Other adjuvants which may be used are alcohol ethoxylates, alkyl polysaccharides, fatty amine ethoxylates, sorbitan and sorbitol ethoxylate derivatives and derivatives of alk(en)ylsuccinic anhydride.

The mixing ratio of these adjuvants to the copolymers is preferably in the range 1:10 to 10:1.

Suitable binders for solid formulations are polyvinylpyrrolidone, polyvinyl alcohol, carboxymethylcellulose, sugars, for example sucrose, sorbitol, or starch.

Suitable thinners, absorbers or carriers are carbon black, tallow, kaolin, aluminum stearate, calcium stearate or magnesium stearate, sodium tripolyphosphate, sodium tetraborate, sodium sulfate, silicates and sodium benzoate.

Suitable disintegrants are cellulose, for example carboxymethylcellulose, polyvinylpyrrolidone, sodium acetate or potassium acetate, carbonates, bicarbonates, sesquicarbonates, ammonium sulfate or potassium hydrogenphosphate.

Wetting agents which may be used are alcohol ethoxylates/propoxylates.

The pesticide preparations preferably have a pH of from 4 to 8, particularly preferably 6 to 7.

The formulations according to the invention can be used in accordance with customary methods.

Aqueous concentrates and solid formulations are diluted with the corresponding amount of water prior to application. Preferably, 0.1 to 5 kg, preferably 0.3 to 2.5 kg, of pesticide are applied per hectare. The proportion of the copolymers is preferably 0.1 to 3.0 kg/ha. The amount of pesticide preparation for spray application is preferably 50 to 1000 l/ha.

The properties of the copolymers or pesticide preparations, such as, for example, solubility in water, electrolyte stability, viscosity and compatibility with crop protection agent active ingredients can advantageously be very readily set via the degree of crosslinking. For the degree of crosslinking, the nature and content of the dicarboxylic acid component b) are decisive, the content being of particular importance.

Surprisingly, it has been found that high-concentration aqueous formulations of anionic pesticides, in particular glyphosate in salt form, and copolymers are phase stable. Even in cases of prolonged storage period, no crystallization of the ionic components is observed.

In addition to the high electrolyte stability, the use of the copolymers according to the invention effects an improvement in the compatibility and the contactability of the hydrophilic active ingredient with the lipophilic epidermis of the plants.

A good wettability and absorption capacity of the pesticide formulations according to the invention aids the bioactivity in the active ingredient in the plants.

The invention also provides a method of increasing the bioactivity of pesticides, which involves using the pesticides in the form of pesticide preparations comprising copolymers obtainable by copolymerization of a) glycerol
b) at least one dicarboxylic acid and
c) at least one monocarboxylic acid according to formula (I).

The method is preferably suitable for herbicides, in particular for glyphosate, and salts and/or derivatives thereof.

EXAMPLES

The examples below demonstrate the influence of the copolymers on the bioactivity of the herbicide glyphosate.

1) Preparation of the Copolymers I to V

Preparation of Polyglycerol where n=9.7:

2000 g of glycerol and 6.0 g of NaOH (50%) were heated to 270° C. in a stirred apparatus with nitrogen introduction and water separator with stirring. After a reaction time of 9 hours and a discharge of 444 g of water, a sample was taken and the OH number was determined. The OH number determined was 891 mg of KOH/g. This corresponds to an average degree of condensation n of 9.7 glycerol units. The degree of condensation can also be determined approximately via the viscosity or the refractive index of the reaction mixture. For this purpose, it is necessary to construct a calibration curve beforehand.

Preparation of Copolymer I:

180.00 g of polyglycerol n=9.7 (0.243 mol) were added to a stirred container with $N_2$ introduction and water separator and treated with 24.70 g of coconut fatty acid ($C_8/C_{18}$) (0.121 mol) and 10.13 g of phthalic acid (0.061 mol). The reaction mixture was then heated, with stirring, at 220° C. for 7 hours. The copolymer had an acid number of 0.40 mg of KOH/g.

Preparation of Copolymer II:

190.00 g of polyglycerol where n=9.7 (0.256 mol) were introduced into a stirred container with $N_2$ introduction and water separator and treated with 26.11 g of coconut fatty acid ($C_8/C_{18}$) (0.128 mol) and 4.32 g of phthalic acid (0.026 mol). The reaction mixture was then heated at 220° C. for 7 hours with stirring. The copolymer had an acid number of 0.46 mg of KOH/g.

Preparation of Copolymer III:

185.00 g of polyglycerol where n=9.7 (0.256 mol) were introduced into a stirred container with $N_2$ introduction and water separator and treated with 4.25 g of phthalic acid (0.0256 mol) for two hours at 215° C. The reaction mixture was clear and homogenous. 25.50 g of coconut fatty acid ($C_8/C_{18}$) (0.125 mol) were then introduced into the stirred container and reacted for 5 hours at 215° C. The copolymer had an acid number of 0.38 mg of KOH/g.

Copolymer IV:

185.00 g of polyglycerol where n=9.7 (0.256 mol) were introduced into a stirred container with $N_2$ introduction and water separator and crosslinked with 10.38 g of phthalic acid (0.0625 mol) for two hours at 215° C. The reaction mixture was clear and homogeneous. 25.50 g of coconut fatty acid ($C_8/C_{18}$) (0.125 mol) were introduced into the stirred container and reacted for 5 hours at 215° C. The copolymer had an acid number of 0.53 mg of KOH/g.

Copolymer V:

180.00 g of polyglycerol where n=9.7 (0.243 mol) were introduced into a stirred container with $N_2$ introduction and water separator and esterified with 24.75 g of coconut fatty acid ($C_8/C_{18}$) (0.121 mol), an acid number of 0.14 mg of KOH/g being achieved after 5 hours and an esterification temperature of 215° C. 4.03 g of phthalic acid were then added and crosslinked for 2 hours at 215° C. The reaction end-product was clear and homogenous.

Preparation of test formulations comprising the copolymers I to V

Test formulations were prepared with in each case 200 g, 300 g and 500 g of glyphosate and in each case 600 g of the copolymers I to V in 300 l of water. The data by weight refer to 100% active ingredient and 100% adjuvant. An amount of the formulation corresponding to the ratio 300 l/ha was applied in a greenhouse to the plant species *Abutilon theophrasti* (ABUTH), *Sesbania exaltata* (SEBEX), *Pharbitis purpurea* (PHBPU), *Galium aparine* (GALAP), *Amaranthus retroflexus* (AMARE) and *Echinochloa crus-galli* (ECHCG), and, after 21 days at 20° C., the plant growth was assessed according to a % scale.

0% means no effect and 100% means complete destruction of the types of plant. The effect of the copolymers I to V on the herbicidal action of glyphosate is shown in Table 1.

TABLE 1

Effect of the copolymers I-V on the herbicidal action of glyphosate

| Glyphosate (g/ha) | Copolymers | SEBEX | AMARE | GALAP | ABUTH | ECHCG | PHBPU | Total |
|---|---|---|---|---|---|---|---|---|
| 200 | — | 10 | 20 | 5 | 0 | 15 | 10 | 10 |
| 300 | — | 15 | 45 | 20 | 10 | 20 | 20 | 22 |
| 500 | — | 30 | 65 | 40 | 15 | 40 | 40 | 38 |
| 200 | I | 75 | 80 | 25 | 20 | 70 | 45 | 53 |
| 300 | I | 85 | 85 | 50 | 55 | 85 | 65 | 70 |
| 500 | I | 95 | 90 | 75 | 75 | 90 | 85 | 85 |
| 200 | II | 35 | 70 | 45 | 25 | 65 | 30 | 45 |
| 300 | II | 50 | 85 | 70 | 50 | 80 | 55 | 65 |
| 500 | II | 90 | 95 | 80 | 70 | 95 | 80 | 85 |
| 200 | III | 40 | 65 | 35 | 20 | 60 | 20 | 40 |
| 300 | III | 65 | 80 | 60 | 50 | 70 | 35 | 60 |
| 500 | III | 85 | 85 | 70 | 65 | 85 | 55 | 74 |
| 200 | IV | 45 | 70 | 55 | 30 | 45 | 30 | 46 |
| 300 | IV | 65 | 85 | 65 | 50 | 65 | 50 | 63 |
| 500 | IV | 95 | 90 | 70 | 65 | 90 | 80 | 82 |
| 200 | V | 35 | 70 | 25 | 15 | 50 | 35 | 38 |
| 300 | V | 50 | 85 | 45 | 40 | 75 | 65 | 60 |
| 500 | V | 60 | 95 | 70 | 65 | 90 | 95 | 79 |

It is clear that the copolymers effected a significant increase in the herbicidal action of glyphosate.

The invention claimed is:

1. A pesticide preparation comprising at least one pesticide and at least one copolymer obtained by copolymerization of
   a) glycerol,
   b) at least one dicarboxylic acid, and
   c) at least one monocarboxylic acid of the formula (I)

$$R^1\text{—COOH} \qquad (I)$$

where $R^1$ is ($C_5$-$C_{29}$)-alkyl; ($C_7$-$C_{29}$)-alkenyl; phenyl or naphthyl, wherein the copolymers comprise 19.9 to 99% by weight of component a), 0.1 to 30% by weight of component b) and 0.9 to 80% by weight of component c).

2. The pesticide preparation as claimed in claim 1, wherein the dicarboxylic acid b) is oxalic acid; a dicarboxylic acid according to formula (II)

$$\text{HOOC—}R^2\text{—COOH} \qquad (II)$$

and/or a dicarboxylic acid according to formula (III)

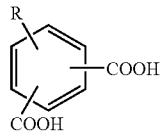

wherein
$R^2$ is a $(C_1\text{-}C_{40})$-alkylene bridge or a $(C_2\text{-}C_{20})$-alkenylene bridge and
R is one or more radicals selected from the group consisting of H, $(C_1\text{-}C_{20})$-alkyl, $(C_2\text{-}C_{20})$-alkenyl, phenyl, benzyl, halogen, —$NO_2$, $(C_1\text{-}C_6)$-alkoxy, —CHO, —CO$((C_1\text{-}C_6)$-alkyl), and mixtures thereof.

3. The pesticide preparation as claimed in claim 1, wherein the dicarboxylic acid b) is selected from the group consisting of oxalic acid, malonic acid, succinic acid, glutaric acid, adipic acid, pimelic acid, suberic acid, fumaric acid, malic acid, phthalic acid, isophthalic acid, terephthalic acid, and mixtures thereof.

4. The pesticide preparation as claimed in claim 1, wherein the dicarboxylic acid b) is selected from the group consisting of phthalic acid, isophthalic acid, terephthalic acid, and mixtures thereof.

5. The pesticide preparation of claim 1, wherein the monocarboxylic acid c) is a fatty acid or a mixture of fatty acids.

6. The pesticide preparation of claim 1, wherein the monocarboxylic acid c) is selected from the group consisting of coconut acid, tallow fatty acid, and mixtures thereof.

7. The pesticide preparation of claim 1, wherein the dicarboxylic acid b) is phthalic acid and the monocarboxylic acid c) is coconut fatty acid.

8. The pesticide preparation of claim 1, wherein the copolymer comprises 1 to 10% by weight of component b).

9. The pesticide preparation of claim 1, wherein the copolymers have an OH number of from 400 to 1000 mg of KOH/g.

10. The pesticide preparation of claim 1, wherein the copolymer comprises a viscosity at 60° C. in the range of 1500 mPas to 35000 mPas.

11. The pesticide preparation of claim 1, wherein during the copolymerization, firstly the glycerol component a) is polymerized to a polyglycerol, and then the polyglycerol and a mixture of the dicarboxylic acid component b) and the monocarboxylic acid component c) are copolymerized.

12. The pesticide preparation of claim 1, wherein the glycerol component a) is firstly polymerized to polyglycerol, then the dicarboxylic acid component b) is copolymerized and then the monocarboxylic acid component c) is copolymerized.

13. The pesticide preparation of claim 1, wherein the glycerol component a) is firstly polymerized to polyglycerol, then the monocarboxylic acid component c) is copolymerized and then the dicarboxylic acid component b) is copolymerized.

14. The pesticide preparation of claim 1, wherein the pesticide is selected from the group consisting of herbicides, insecticides, fungicides, bactericides, molluscicdes, nematicides, rodenticides, and mixtures thereof.

15. The pesticide preparation of claim 1, wherein the pesticide is an herbicide.

16. The pesticide preparation of claim 15, wherein the herbicide is selected from the group consisting of glyphosate, glyphosate salts, and mixtures thereof.

17. The pesticide preparation of claim 1, which is in a form selected from the group consisting of a "tank-mix", "ready to use composition", concentrate, powder, pellet, tablet, and granulate.

18. A method for increasing the bioactivity of at least one pesticide, said method comprising adding to the pesticide at least one copolymer obtained by copolymerization of
a) glycerol,
b) at least one dicarboxylic acid, and
c) at least one monocarboxylic acid of the formula (I)

$$R^1\text{—COOH} \qquad (I)$$

where $R^1$ is $(C_5\text{-}C_{29})$-alkyl: $(C_7\text{-}C_{29})$-alkenyl; phenyl or naphthyl, wherein the copolymers comprise 19.9 to 99% by weight of component a), 0.1 to 30% by weight of component b) and 0.9 to 80% by weight of component c).

19. The pesticide preparation as claimed in claim 1, wherein the dicarboxylic acid b) is phthalic acid.

20. The pesticide preparation of claim 1, wherein the monocarboxylic acid c) is coconut acid.

21. The pesticide preparation as claimed in claim 1, wherein the pesticide preparation is in the form of a concentrate formulation having from 5 to 60% by weight of the pesticide and from 3 to 50% by weight of the copolymer.

22. The pesticide preparation of claim 21 wherein the concentrate formulation has a weight ratio of copolymer to pesticide of from 1:20 to 1:1.

23. The pesticide preparation of claim 21 wherein the concentrate formulation is a phase stable aqueous concentrate.

* * * * *